United States Patent [19]
Braun

[11] Patent Number: 6,102,974
[45] Date of Patent: Aug. 15, 2000

[54] DYEING AGENT FOR DYEING KERATIN FIBRES

[75] Inventor: Hans-Juergen Braun, Ueberstorf, Switzerland

[73] Assignee: Wella Aktiengesellschaft, Darmstadt, Germany

[21] Appl. No.: 09/077,143

[22] PCT Filed: Sep. 29, 1997

[86] PCT No.: PCT/EP97/05336

§ 371 Date: May 21, 1998

§ 102(e) Date: May 21, 1998

[87] PCT Pub. No.: WO98/19659

PCT Pub. Date: May 14, 1998

[30] Foreign Application Priority Data

Nov. 5, 1996 [DE] Germany .................. 196 45 540

[51] Int. Cl.$^7$ ................................. A61K 7/13
[52] U.S. Cl. .................. 8/411; 8/407; 8/408; 8/411; 8/412; 8/414; 8/416; 8/421
[58] Field of Search ................. 8/407, 408, 411, 8/412, 414, 416, 421

[56] References Cited

U.S. PATENT DOCUMENTS

| | | | |
|---|---|---|---|
| 5,067,966 | 11/1991 | Mager et al. ................. | 8/405 |
| 5,518,507 | 5/1996 | Audousset et al. ........... | 8/411 |
| 5,849,041 | 12/1998 | Kunz et al. ................... | 8/408 |
| 5,863,300 | 1/1999 | Audouset et al. ............. | 8/411 |

FOREIGN PATENT DOCUMENTS

| | | |
|---|---|---|
| 0 665 005 B1 | 8/1995 | European Pat. Off. . |
| 706787 | 4/1996 | European Pat. Off. . |
| 3834142 | 4/1990 | Germany . |
| 3942294 | 6/1991 | Germany . |

*Primary Examiner*—Caroline D. Liott
*Attorney, Agent, or Firm*—Michael J. Striker

[57] ABSTRACT

The hair dye composition contains a combination of oxidation dye precursors consisting of (a) 2-hydroxymethyl-p-phenylenediamine, 2-(2',5'-diaminophenyl)ethanol and/or 2-(2'-hydroxyethoxy)-p-phenylenediamine, (b) 2-(2',4'-diaminophenoxy)-ethanol, 1,3-bis-(2',4'-diaminophenoxy) propane, bis-(2',4'-diamino-phenoxy)-methane, 2-amino-4-((2'-hydroxyethyl)amino)-anisole, 1-(2'-aminoethoxy)-2,4-diaminobenzene, 2-(2'-hydroxyethoxy)-5-(methylamino) aniline, 2,4-diamino-1,5-bis-(2'-hydroxyethoxy)benzene and/or 1-(2',3'-dihydroxypropoxy)-2,4-diaminobenzene; and (c) at least one 2-amino-6-chloro-4-nitrophenol compound having the general formula (1):

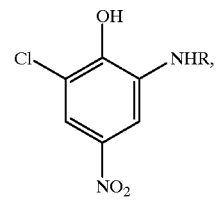

I wherein R represents hydrogen a straight-or branched-chain alkyl group with 1 to 6 carbon atoms, a hydroxyalkyl group with 2 to 4 carbon atoms or a straight or branched-chain polyhydroxyalkyl group with 3 to 4 carbon atoms. A method of dyeing hair with this hair dye composition is also disclosed, which provides uniform dyeing of hair without mutagenic and sensitizing effects.

13 Claims, No Drawings

DYEING AGENT FOR DYEING KERATIN FIBRES

BACKGROUND OF THE INVENTION

The present invention describes a composition for dyeing keratinic fibers, particularly human hair, containing one monosubstituted p-phenylenediamine on a benzene ring, a substituted m-phenylenediamine and a 2-amino-6-chloro-4-nitrophenol derivative.

In the field of hair coloring, oxidation dye compositions have gained major importance. With them, the dyeing develops by way of a reaction of certain developer substances with certain coupler substances in the presence of an oxidant.

Oxidation dye compositions to be used to dye human hair must meet many requirements. The compositions must be toxicologically and dermatologically harmless as well as non-sensitizing and have to allow for the desired intensity in dye.

In addition, the hair dyes sought must have good light fastness, permanent wave fastness, and resistance to acid and abrasion. Even without the exposure to light, abrasion and chemical agents, the result of the dyeing should hold its color for at least four to six weeks. In addition, it is necessary, that through the use of appropriate developer and coupler components a broad spectrum of different color nuances can be achieved.

Another problem in practice is the different absorption of the dye compounds as a function of the nature of the hair, which results in uneven coloring of the hair. Normally, the dye compounds used tend to be absorbed more strongly by damaged parts of the hair than undamaged parts of the hair. For this reason, as a rule, the ends of the hair, which are more heavily damaged by typical aging processes and environmental factors (such as sunlight, hair washing, dyeing and permanent waving treatments), are dyed more intensively than the less-damaged shafts of the hair and the hairline, and the result is an unnatural, uneven and entirely unsatisfactory outcome of dyeing. This situation is particularly annoying with light shades.

SUMMARY OF THE INVENTION

It is therefore an object of the present invention to furnish an oxidative hair dye that enables uniform dyeing of the hair from the ends to the hairline within the natural range of shades, and at the same time that is only slightly mutagenic and sensitizing, if at all, and is highly biocompatible.

In European Patent Disclosure EP 0 665 005, the combination of a monosubstituted p-phenylenediamine benzene ring and a substituted m-phenylenediamine has been recommended for the dyeing of hair. This combination, however, provides unsatisfactory coloring results on unevenly damaged hair. In addition, the gradation of lighter shades in this case are more difficult to achieve.

Surprisingly it now has been found that the described disadvantages can be avoided, if the oxidative hair dye composition comprises a combination of oxidation dye precursors comprising at least one p-phenylenediamine derivative compound, selected from the group consisting of
2-hydroxymethyl-p-phenylenediamine,
2-(2',5'-diaminophenyl)ethanol, and
2-(2'-hydroxyethoxy)-p-phenylenediamine,
at least one m-phenylenediamine derivative compound, selected from the group consisting of
2-(2',4'-diaminophenoxy)ethanol,
1,3-bis-(2',4'-diaminophenoxy)propane,
bis-(2',4'-diaminophenoxy)methane,
2-amino-4-((2'-hydroxyethyl)amino)anisole,
1-(2'-aminoethoxy)-2,4-diaminobenzene,
2-(2'-hydroxyethoxy)-5-(methylamino)aniline,
2,4-diamino-1,5-bis-(2'-hydroxyethoxy)benzene, and
1-(2'3'-dihydroxypropoxy)-2,4-diaminobenzene, and
at least one 2-amino-6-chloro-4-nitrophenol compound in accordance with the general formula (I),

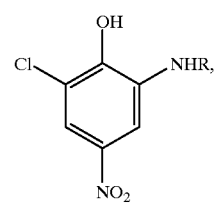

in which R stands for hydrogen, a straight- or branched-chain alkyl group with 1 to 6 carbon atoms, a hydroxyalkyl group with 2 to 4 carbon atoms, or a straight- or branched-chain polyhydroxyalkyl group with 3 to 4 carbon atoms.

Preferred derivatives in accordance with general formula (I) are: 2-amino-6-chloro-4-nitrophenol, 6-chloro-2-ethylamino-4-nitrophenol and 6-chloro-2-((2'-hydroxyethyl)amino-4-nitrophenol.

The dye combination described makes even dyeing from the hairline to the ends of the hair possible, especially with lighter shades. The superior properties of the novel dye combination are exhibited especially in hair damaged by light and weather or in permanent-waved hair.

To round out the outcome of dyeing and to create special color effects, other oxidation dye precursors can be added to the hair dye, such as resorcinol, 4-chlororesorcinol, and derivatives of m-aminophenols, other p-phenylenediamine derivative compounds, and 1,3-benzenedioxol derivative compounds, as well as direct dyes, such as azo dyes, anthraquinones or nitrobenzene derivatives.

For the purpose of dyeing, the above-described combination of oxidation dye precursors in accordance with the invention and optionally direct dyes are applied in a suitable dye composition.

The subject of the present application therefore also relates to a means for oxidatively dyeing hair, which is prepared by mixing a dye composition with an oxidant immediately prior to use.

The dye composition according to the invention contains the above-described combinations either per se or in form of biocompatible salts, for example inorganic or organic acid addition salts such as hydrochlorides, sulfates or tartrates, or in the case of phenols, alkali phenolates.

The total concentration of color precursors is approximately 0.1 to 10 weight %, and preferably 0.2 to 6 weight %.

In addition, typical cosmetic additives can also be contained in the dye composition, examples being such antioxidants as ascorbic acid, thioglycolic acid or sodium sulfite; perfume oils; complexing agents; wetting agents; emulsifiers; thickeners; conditioners, and others.

The form of preparation both for the dye composition and for the oxidative hair dye that is ready to use may for example be a solution, and in particular an aqueous or aqueous-alcohol solution. The particularly preferred forms of preparation, however, are a cream, gel, or emulsion. Their composition represents a mixture of the dye components with the additives typical for such preparations.

Conventional additives in solutions, creams, emulsions, or gels are for example solubilizers with water, low aliphatic alcohols, such as ethanol, n-propanol and isopropanol, or glycols such as glycerin and 1,2-propylene glycol, and also neutralizers or emulsifiers selected from the anionic, cationic, amphoteric or non-ionic classes of surfactants, such as fatty alcohol sulfates, ethoxylated fatty alcohol sulfates, alkyl sulfonates, alkyl benzene sulfonates, alkyltrimethylammonium salts, alkyl betaines, ethoxylated fatty alcohols, ethoxylated nonylphenols, fatty acid alkanolamides, ethoxylated fatty alcohols, ethoxylated nonylphenols, fatty acid alkanolamides, ethoxylated fatty esters; also thickeners, such as higher fatty alcohols, starch or cellulose derivatives; and vaseline, paraffin oil and fatty acids, as well as conditioners such as cationic resins, lanolin derivatives, cholesterol, pantothenic acid and betaine. The aforementioned ingredients are used in the customary quantities for such purposes, for example the neutralizers and emulsifiers in a concentration of approximately 0.5 to 30 weight-percent (referred to the dye composition), the thickeners in a quantity of approximately 0.1 to 25 weight-percent (referred to the dye composition) and the conditioners in a concentration of approximately 0.1 to 5.0 weight-percent (referred to the dye composition).

The ready-to-use hair dye in accordance with the invention is prepared immediately before use by mixing the dye composition with a liquid oxidant.

The dye composition and the oxidant in this case are mixed together in a weight ratio of 5:1 to 1:3, with a weight ratio of 1:1 to 1:2 being especially preferred.

In the mixing of the preferably alkaline dye composition, the pH value of the ready-to-use hair dye according to the invention is adjusted by means of the usually acidic oxidant to a pH value that is determined by the quantity of alkali in the dye composition and of acid in the oxidant, and by the mixture ratio. The pH value of the finished hair dye is from 3 to 11, and preferably 5 to 9.

For adjusting the pH value of the dye composition and the oxidant, one can use organic and inorganic acids such as phosphoric acid, ascorbic acid and lactic acid, or alkalis such a monoethanolamine, triethanolamine, 2-amino-2-methyl-1-propanol, ammonia, soda lye, potash lye, or tris (hydroxymethyl)aminomethane, depending on the desired pH value.

For use in oxidative hair coloring, the above-described dye composition is mixed with an oxidant immediately before use, and an appropriate amount of the ready-to-use oxidative hair dye obtained that is suitable for the hair coloring treatment is applied to the hair, generally from about 60 to 200 grams, depending on the fullness of the hair.

As an oxidant, especially hydrogen peroxide, or its addition compounds of uric acid, melamine, or sodium bromate, in the form of a 1 to 12 percent, and preferably a 6 percent aqueous solution, can be considered; hydrogen peroxide is particularly preferred.

The hair dye in accordance with the invention is left to act on the hair for approximately 10 to 45 minutes at 15 to 50° C., preferably for 30 minutes; the hair is then rinsed with water and dried. If necessary, the hair may be washed with a shampoo after rinsing, and/or may be re-rinsed with a weak organic acid, such as citric acid or tartaric acid. The hair is then dried.

The following examples are intended to explain the invention in further detail, without limiting it to these examples.

EXAMPLES

Example 1: Hair Dye Solution

| | |
|---|---|
| 0.2 g | 2-(2'5'-diaminophenyl) ethanolsulfate |
| 0.1 g | 2-(2,4-diaminophenoxy) ethanol dihydrochloride |
| 0.4 g | 2-Amino-6-chloro-4-nitrophenol |
| 10.0 g | Isopropanol |
| 10.0 g | Lauryl alcohol diglycolic ether sulfate sodium salt (28-percent aqueous solution) |
| 10.0 g | Ammonia (25-percent aqueous solution) |
| 0.3 g | Ascorbic acid |
| 69.0 g | Water, fully desalinated |
| 100.0 g | |

Prior to use, 10 g hair coloring solution are mixed with 10 g hydrogen peroxide solution (6-percent aqueous solution). The resulting ready-to-use oxidative hair coloring agent is applied to hair damaged by wind and weather. After a reaction time of 30 minutes at 40° C. the hair is rinsed, shampooed and dried.

The hair has received an even brown tone.

Example 2: Cream Hair Dye

| | |
|---|---|
| 0.3 g | 2-Hydroxymethyl-p-phenylenediamine sulfate |
| 0.1 g | 1,3-Bis(2,4-diaminophenoxy)propane tetrahydrochloride |
| 0.2 g | 2-Chloro-6-(ethylamino)-4-nitrophenol |
| 15.0 g | Cetyl alcohol |
| 3.5 g | Lauryl alcohol diglycolic ether sulfate sodium salt (28-percent aqueous solution) |
| 3.0 g | Ammonia (25-percent aqueous solution) |
| 0.3 g | Sodium sulfite, non-aqueous |
| 77.3 g | Water, fully desalinated |
| 100.0 g | |

Prior to use, 10 g hair coloring solution are mixed with 10 g hydrogen peroxide solution (6-percent aqueous solution). The resulting ready-to-use oxidative hair coloring agent is applied to hair damaged by wind and weather. After a reaction time of 30 minutes at 40° C. the hair is rinsed, shampooed and dried.

The hair is dyed an even red-brown tone from the hairline to the ends.

Example 3: Hair Dye Solution

| | |
|---|---|
| 0.6 g | 2,5-Diaminoanisole |
| 0.6 g | 2-(2',4'-Diaminophenoxy)ethanol dihydrochloride |
| 0.2 g | 6-Chloro-2-((2'-hydroxyethyl)amino)-4-nitrophenol |
| 10.0 g | Isopropanol |
| 10.0 g | Lauryl alcohol diglycolic ether sulfate sodium salt (28-percent aqueous solution) |
| 10.0 g | Ammonia (25-percent aqueous solution) |
| 0.3 g | Ascorbic acid |
| 68.3 g | Water, fully desalinated |
| 100.0 g | |

Prior to use, 10 g hair coloring solution are mixed with 10 g hydrogen peroxide solution (6-percent aqueous solution). The resulting ready-to-use oxidative hair coloring agent is applied to hair damaged by wind and weather. After a reaction time of 30 minutes at 40° C. the hair is rinsed, shampooed and dried.

The hair has received an even black tone.

All percentages given represent weight-percent, unless otherwise indicated.

I claim:

1. A hair dye composition for dyeing hair, said hair dye composition comprising a combination of oxidation dye precursors, said oxidation dye precursors comprising
   at least one p-phenylenediamine derivative compound selected from the group consisting of 2-hydroxymethyl-p-phenylenediamine, 2-(2',5'-diamino-phenyl)ethanol and 2-(2'-hydroxyethoxy)-p-phenylenediamine;
   at least one m-phenylenediamine derivative compound selected from the group consisting of 2-(2',4'-diaminophenoxy)-ethanol, 1,3-bis-(2',4'-diamino-phenoxy)propane, bis-(2',4'-diamino-phenoxy)-methane, 2-amino-4-((2'-hydroxyethyl)amino)anisole, 1-(2'-aminoethoxy)-2,4-diaminobenzene, 2-(2'-hydroxyethoxy)-5-(methylamino)aniline, 2,4-diamino-1,5-bis-(2'-hydroxyethoxy)-benzene and 1-(2',3'-dihydroxypropoxy)-2,4-diaminobenzene; and
   at least one 2-amino-6-chloro-4-nitrophenol compound having the general formula (1):

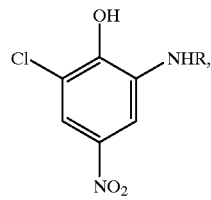

I wherein R represents hydrogen, a straight- or branched-chain alkyl group with 1 to 6 carbon atoms, a hydroxyalkyl group with 2 to 4 carbon atoms or a straight or branched-chain polyhydroxyalkyl group with 3 to 4 carbon atoms.

2. The hair dye composition as defined in claim 1, wherein the at least one 2-amino-6-chloro-4-nitrophenol compound is selected from the group consisting of 2-amino-6-chloro-4-nitrophenol, 6-chloro-2-ethyl-amino-4-nitrophenol and 6-chloro-2-((2'-hydroxyethyl)amino)-4-nitrophenol.

3. The hair dye composition as defined in claim 1, further comprising, in addition to said combination of said oxidation dye precursors, at least one other oxidation dye precursor selected from the group consisting of p-phenylenediamine derivative compounds other than said 2-hydroxymethyl-p-phenylenediamine, said 2-(2',5'-diaminophenyl)ethanol and said 2-(2'-hydroxyethoxy)-p-phenylenediamine; resorcinol derivative compounds and 1,3-benzenedioxol derivative compounds.

4. The hair dye composition as defined in claim 1, further comprising at least one direct-dyeing dye compound in addition to said oxidation dye precursors.

5. The hair dye composition as defined in claim 1, wherein said at least one p-phenylenediamine derivative compound, said at least one m-phenylene-diamine derivative compound and said at least one 2-amino-6-chloro-4-nitrophenol compound are present in the form of addition salts thereof with an inorganic or organic acid.

6. The hair dye composition as defined in claim 1, further comprising a cosmetic vehicle.

7. The hair dye composition as defined in claim 3, containing a total concentration of 0.1 to 10 weight percent of said oxidation dye precurors.

8. The hair dye composition as defined in claim 1, further comprising at least one conventional cosmetic additive.

9. A ready-to-use hair dyeing mixture made by mixing a hair dye composition with an oxidant immediately prior to application;

wherein said hair dye composition comprises a combination of oxidation dye precursors comprising of:
   at least one p-phenylenediamine derivative compound selected from the group consisting of 2-hydroxymethyl-p-phenylenediamine, 2-(2',5'-diamino-phenyl)ethanol and 2-(2'-hydroxyethoxy)-p-phenylenediamine;
   at least one m-phenylenediamine derivative compound selected from the group consisting of 2-(2',4'-diaminophenoxy)-ethanol 1,3-bis-(2',4'-diamino-phenoxy)propane, bis-(2',4'-diamino-phenoxy)-methane, 2-amino-4-((2'-hydroxyethyl)amino)anisole, 1-(2'-aminoethoxy)-2,4-diaminobenzene, 2-(2'-hydroxyethoxy)-5-(methylamino)aniline, 2,4-diamino-1,5-bis-(2'-hydroxyethoxy)-benzene and 1-(2',3'-dihydroxypropoxy)-2,4-diaminobenzene; and
   at least one 2-amino-6-chloro-4-nitrophenol compound having the general formula (1):

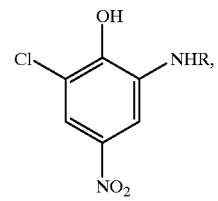

I wherein R represents hydrogen, a straight- or branched-chain alkyl group with 1 to 6 carbon atoms, a hydroxyalkyl group with 2 to 4 carbon atoms or a straight or branched-chain polyhydroxyalkyl group with 3 to 4 carbon atoms.

10. The ready-to-use hair dyeing mixture as defined in claim 9, wherein said hair dye composition is mixed with said oxidant in a weight ratio of 5:1 to 1:3.

11. The ready-to-use hair dyeing mixture as defined in claim 9, having a pH value of from 3 to 11.

12. A method for oxidative dyeing hair, said method comprising the steps of:
   a) mixing a hair dye composition with an oxidant in a weight ratio of 5:1 to 1:3 to form a ready-to-use hair dyeing mixture having a pH of from 3 to 11;
   b) applying a sufficient amount of said ready-to-use hair dyeing mixture to the hair to dye the hair,
   c) after the applying, allowing said ready-to-use hair dyeing mixture to act on the hair at a temperature of 15 to 50° C. for 10 to 45 minutes; and
   d) subsequently rinsing the hair with water and then drying the hair;
   wherein said hair dye composition comprises a combination of oxidation dye precursors, said combination comprising:

at least one p-phenylenediamine derivative compound selected from the group consisting of 2-hydroxymethyl-p-phenylenediamine, 2-(2',5'-diamino-phenyl)ethanol and 2-(2'-hydroxyethoxy)-p-phenylenediamine, at least one m-phenylenediamin a derivative compound selected from the group consisting of 2-(2',4'-diaminophenoxy)-ethanol, 1,3-bis-(2',4'-diamino-phenoxy)propane, bis-(2',4'-diamino-phenoxy)-methane, 2-amino-4-((2'-hydroxyethyl)amino)anisole, 1-(2'-aminoethoxy)-2,4-diaminobenzene, 2-(2'-hydroxyethoxy)-5-(methylamino)aniline, 2,4-diamino-1,5-bis-(2'-hydroxyethoxy)-benzene and 1-(2',3'-dihydroxypropoxy)-2,4-diaminobenzene; and at least one 2-amino-6-chloro-4-nitrophenol compound having the general formula (1):

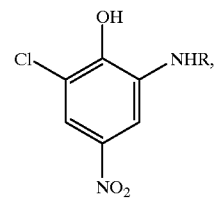

wherein R represents hydrogen, a straight- or branched-chain alkyl group with 1 to 6 carbon atoms, a hydroxyalkyl group with 2 to 4 carbon atoms or a straight or branched-chain polyhydroxyalkyl group with 3 to 4 carbon atoms.

13. The method as defined in claim 12, further comprising after the allowing, shampooing the hair.

\* \* \* \* \*